United States Patent [19]

Hara et al.

[11] Patent Number: 5,286,906
[45] Date of Patent: Feb. 15, 1994

[54] PROCESS FOR THE PREPARATION OF 3-AMINOMETHYL-3,5,5-TRIALKYLCYCLOHEXYLAMINE

[75] Inventors: Yoshinori Hara; Haruhiko Kusaka, both of Tokyo; Masamichi Onuki, Kanagawa; Sugio Nishimura, Tokyo, all of Japan

[73] Assignee: Mitsubishi Kasei Corporation, Tokyo, Japan

[21] Appl. No.: 950,688

[22] Filed: Sep. 25, 1992

[30] Foreign Application Priority Data

Sep. 25, 1991 [JP] Japan ............... 3-246115
May 22, 1992 [JP] Japan ............... 4-154160

[51] Int. Cl.$^5$ ............... C07C 209/22; C07C 209/48
[52] U.S. Cl. ............... 564/446; 564/448; 564/455
[58] Field of Search ............... 564/448, 493, 446, 455

[56] References Cited

U.S. PATENT DOCUMENTS

| | | | |
|---|---|---|---|
| 2,449,036 | 9/1948 | Grunfeld | 564/493 |
| 3,352,913 | 11/1967 | Schmitt et al. | 564/455 |
| 3,372,195 | 3/1968 | Little | 564/493 |
| 3,880,929 | 4/1975 | Drake | 564/491 |
| 4,003,933 | 1/1977 | Drake | 564/448 |
| 4,235,821 | 11/1980 | Butte, Jr. et al. | 564/493 |
| 4,429,157 | 1/1984 | Disteldorf et al. | 564/446 |
| 5,166,396 | 11/1992 | Hutchmacher et al. | 558/431 |
| 5,166,444 | 11/1992 | Hutchmacher et al. | 564/491 |

FOREIGN PATENT DOCUMENTS

| | | |
|---|---|---|
| 2062267 | 9/1992 | Canada . |
| 0284398 | 9/1988 | European Pat. Off. . |
| 394967 | 10/1990 | European Pat. Off. . |
| 0394968 | 10/1990 | European Pat. Off. . |
| 0449089 | 10/1991 | European Pat. Off. . |
| 3011656 | 10/1981 | Fed. Rep. of Germany . |
| 62-123154 | 4/1987 | Japan . |
| 4-221350 | 8/1992 | Japan . |
| 4-264057 | 9/1992 | Japan . |
| 4-338365 | 11/1992 | Japan . |
| 972010 | 10/1964 | United Kingdom . |

*Primary Examiner*—Richard L. Raymond
*Assistant Examiner*—Scott C. Rand
*Attorney, Agent, or Firm*—Sughrue, Mion, Zinn, Macpeak & Seas

[57] ABSTRACT

A process for the preparation of a 3-aminomethyl-3,5,5-trialkylcyclohexylamine, which comprises hydrogenating 3-cyano-3,5,5-trialkylcyclohexylamine in the presence of ammonia and a ruthenium-cobalt catalyst.

19 Claims, No Drawings

PROCESS FOR THE PREPARATION OF 3-AMINOMETHYL-3,5,5-TRIALKYLCYCLOHEXYLAMINE

FIELD OF THE INVENTION

The present invention relates to a process for the preparation of a 3-aminomethyl-3,5,5-trialkylcyclohexylamine. More particularly, the present invention relates to improvements in the process for the preparation of a 3-aminomethyl-3,5,5-trialkylcyclohexylamine by hydrogenating 3-cyano-3,5,5-trialkylcyclohexanone in a liquid phase in the presence of ammonia and a catalyst.

A 3-aminomethyl-3,5,5-trialkylcyclohexylamine, e.g., 3-aminomethyl-3,5,5-trimethylcyclohexylamine has excellent properties for an epoxy resin hardener or a starting material of urethane elastomer.

BACKGROUND OF THE INVENTION

As disclosed in JP-B-39-10923 (the term "JP-B" as used herein means an "examined Japanese patent publication"), a process has heretofore been known which comprises the reduction of 3-cyano-3,5,5-trimethylcyclohexanone in the presence of ammonia, a catalyst and hydrogen to produce 3-aminomethyl-3,5,5-trimethylcyclohexylamine. However, the preparation process is disadvantageous in that the reaction occurs under an extremely high pressure and that a silicic acid-supported cobalt catalyst must be reduced and crushed immediately before use.

This reaction is also disadvantageous in that it is extremely difficult to avoid the production of 1,3,3-trimethyl-6-azabicyclo[3,2,1]octane (hereinafter referred to as "bicyclo compound") as a by-product by intramolecular cyclization attributable to the structural characteristics of the starting material as described in JP-A-3-47156 (the term "JP-A" as used herein means an "unexamined published Japanese patent application"). This is a main cause that lowers the yield of the desired compound.

Further, JP-B-62-123154 proposes the use of Raney cobalt catalyst as a catalyst. The use of Raney cobalt catalyst allows the reaction to proceed under mild conditions. However, Raney cobalt catalyst has a problem in that it has the property of catching fire in the air and thus needs to be carefully treated.

Thus, there have been problems which must be solved in the actual industrial process for the preparation of a 3-aminomethyl-3,5,5-trialkylcyclohexylamine.

SUMMARY OF THE INVENTION

An object of the present invention is to provide a process for the preparation of a 3-aminomethyl-3,5,5-trialkylcyclohexylamine using a catalyst which enables an efficient production of the desired material under reaction conditions which are mild as compared with the prior art.

Other objects and effects of the present invention will be apparent from the following description.

The present inventors have made extensive studies to solve the above mentioned problems. As a result, it has been found that the use of a ruthenium-cobalt catalyst, which can be easily treated, enables an efficient production of the desired material under relatively mild reaction conditions.

The present invention relates to a process for the preparation of a 3-aminomethyl-3,5,5-trialkylcyclohexylamine which comprises hydrogenating 3-cyano-3,5,5-trialkylcyclohexanone in the presence of a ruthenium-cobalt catalyst and ammonia.

DETAILED DESCRIPTION OF THE INVENTION

A ruthenium-cobalt catalyst is used in the process of the present invention. In the present invention, the desired compound can effectively be produced by using a combination of ruthenium and cobalt. The form of the catalyst is not particularly limited if ruthenium and cobalt are used in combination. From the standpoint of easy handling and the like of the catalyst, a supported catalyst is preferably used. For example, the catalyst used in the present invention can be prepared by having metallic components of ruthenium and cobalt as starting materials supported on a carrier.

As the metallic components of ruthenium and cobalt used as starting materials, salts of ruthenium and cobalt with mineral acids such as nitric acid, sulfuric acid and hydrochloric acid are generally used. Salts of ruthenium and cobalt with organic acids such as acetic acid, hydroxides, oxides or complex salts of ruthenium and cobalt can also be used.

As the carrier, a porous material made of an inorganic material such as silica, alumina, activated carbon, silica-alumina, magnesia and zirconia are generally used. Among these inorganic porous materials, those made of silica, alumina and activated carbon are particularly preferred, with silica being the most preferred. The grain shape and size of these porous carriers can be arbitrarily selected. These porous carriers may be used in the form of powder. The grain shape of these porous carriers may be sphere.

The amount of ruthenium and cobalt supported on the carrier is not specifically limited. The total amount of ruthenium and cobalt to be supported on the carrier is generally in the range of 0.1 to 40% by weight, preferably 1 to 25% by weight, as calculated in terms of metal.

While ruthenium itself has reaction activity, the addition of cobalt to ruthenium improves the reaction activity and inhibits the production of 1,3,3-trimethyl-6-azabicyclo[3,2,1]octane as a by-product of secondary amine.

The method of having metallic components as starting materials supported on the inorganic porous carrier is not specifically limited. In general, the metallic components can be supported on the inorganic porous carrier by impregnating the inorganic porous carrier with the metallic components according to a known method such as dipping process, ion exchange process and forced supporting process, optionally drying the material, and then fixing the material without eluting the metallic components.

The impregnating process can be effectively accomplished by spraying a solution of the starting materials in water or an organic solvent onto the carrier so that they are supported on the carrier.

After being impregnated with the metallic components as starting materials, the carrier is preferably dried thoroughly at a temperature of 20 to 150° C. under a pressure of from vacuum to ordinary pressure to remove the solvent (water or organic solvent) therefrom.

The fixing of the material can be effected by treating the carrier in an alkaline solution or by calcining the carrier in an atmosphere of an oxygen-containing gas such as air.

The fixing in an alkaline solution can be generally effected by thoroughly spraying a solution of an alkaline compound in an amount of 0.8 equivalents or more into the pores of the carrier.

The alkaline compound may be any substance that is alkaline in an aqueous solution. Examples of such a substance include ammonia; hydroxides such as lithium hydroxide, sodium hydroxide, potassium hydroxide, rubidium hydroxide, cesium hydroxide, magnesium hydroxide, calcium hydroxide, strontium hydroxide and barium hydroxide; and carbonates such as lithium carbonate, sodium carbonate, potassium carbonate, rubidium carbonate, cesium carbonate, magnesium carbonate, calcium carbonate, strontium carbonate, barium carbonate and ammonium carbonate. Other examples of alkaline compounds include hydrogencarbonates such as lithium hydrogencarbonate, sodium hydrogencarbonate, potassium hydrogencarbonate, rubidium hydrogencarbonate and cesium hydrogencarbonate, and organic amines such as methylamine, ethylamine, propylamine, morpholine, pyridine and pyrrolidine. Practically preferred among these alkaline compounds are ammonia, sodium hydroxide and sodium carbonate. As the solvent which dissolves these alkaline compounds therein, any solvent which can dissolve the alkaline compound therein can be used. In particular, water and methanol are preferred.

The porous carrier which has catalytic metals supported thereon by fixation with an alkaline solution has no metallic components that is eluted therefrom even when washed with water, and thus the catalyst can be repeatedly washed. After washing, the catalyst is thoroughly dried at a temperature of 20 to 150° C. under a pressure of from vacuum to ordinary pressure.

The fixing with an alkaline solution and the subsequent washing with water removes halogen derived from the starting material and the like. This sometimes results in reduction in the activity of the catalyst. However, since the removal of halogen can inhibit the corrosion of the reactor, it is very desirable from the industrial point of view.

The fixing by calcining in an atmosphere of an oxygen-containing gas such as air can be effected by calcining the porous carrier impregnated with catalytic metal compounds in the air at a temperature of 100 to 600° C., preferably 200 to 500° C., for 1 to 24 hours.

The catalyst thus prepared is preferably subjected to reduction before use in the hydrogenation reaction of the present invention to enhance the catalytic activity and further improve the fixing strength of the metallic components. The reduction can be accomplished by any known liquid phase or gas phase reduction method. The gas phase reduction is generally effected at a temperature of 100 to 500° C., preferably 200 to 400° C. The liquid phase reduction is preferably effected with an aqueous formaldehyde solution or an aqueous hydrazine solution.

In the present invention, the order of supporting the metallic components on the carrier is not specifically limited. As a simple manner, ruthenium and cobalt may be simultaneously supported on the carrier. However, cobalt is preferably supported on the carrier before or after ruthenium is supported or ruthenium and cobalt are simultaneously supported on the carrier to further inhibit the production of the above mentioned bicyclo compound as a by-product. In other words, at least a part of necessary amount of cobalt is preferably supported on the carrier separately from ruthenium by (1) having cobalt supported on the carrier before or after ruthenium is supported on the carrier or (2) having cobalt supported on the carrier before or after ruthenium and cobalt are simultaneously supported on the carrier. In this case, the amount of cobalt to be supported separately from ruthenium is preferably larger than the amount of cobalt to be supported simultaneously with ruthenium to further enhance the effect of inhibiting the production of the above mentioned bicyclo compound as a by-product.

While the mechanisms of the above phenomena are not clear, it can be expected that cobalt supported on the carrier separately from ruthenium takes part in the inhibition of the production of the bicyclo compound as a by-product. It can also be expected that cobalt supported on the carrier simultaneously with ruthenium takes part in the acceleration of the hydrogenation reaction together with ruthenium.

The present invention provides a process for the preparation of a 3-aminomethyl-3,5,5-trialkylcyclohexylamine by catalytically hydrogenating 3-cyano-3,5,5-trialkylcyclohexanone with ammonia in a liquid phase in the presence of the above mentioned catalyst. The amount of the catalyst to be used is preferably in the range of 5 to 60% by weight based on the weight of 3-aminomethyl-3,5,5-trialkylcylohexylamine.

The 3-cyano-3,5,5-trialkylcyclohexanone as the staring material can be easily prepared from isophorone and prussic acid according to the method described in JP-A-57-116038. The alkyl group contained in the starting material is not specifically limited but is preferably an alkyl group having 1 to 6 carbon atoms.

The catalytic hydrogenation reaction of the present invention is preferably effected in the presence of a solvent. In this case, a solution of a 3-cyano-3,5,5-trialkylcyclohexanone as a starting material in a proper solvent is kept at a predetermined temperature under a predetermined pressure with the above mentioned catalyst and a predetermined proportion of ammonia and hydrogen being introduced thereinto in the fixed bed process, moving bed process, suspended bed process or the like.

The hydrogenation reaction is preferably effected by dissolving the starting material in a solvent, subjecting the solution to heat treatment with ammonia being introduced thereinto, and then hydrogenating the material with a catalyst and hydrogen being introduced thereinto so as to enhance the effect of inhibiting the production of a 3-aminomethyl-3,5,5-trialkylcyclohexanol as a by-product.

The amount of ammonia is generally 1 to 50 times by mol, preferably 1 to 20 times by mol, the amount of the starting material. The reaction pressure (hydrogen partial pressure) is preferably in the range of 20 to 150 atm, more preferably 50 to 100 atm. The reaction temperature is preferably in the range of 50 to 150° C., more preferably in the range of 100 to 140° C. If the reaction temperature is too low, the reaction rate shows a remarkable drop. If the reaction temperature is too high, the by-production of high boiling substances is increased.

Preferred examples of the solvent include an alcohol such as methanol, ethanol, 2-propanol, ethylene glycol and 1,4-butanediol or ether such as dioxane, tetrahydrofuran, diethylene glycol dimethyl ether and 1-methoxy-2-propanol. The amount of the solvent to be used is generally in the range of 1 to 10 times by weight, preferably 3 to 6 times by weight, the starting material.

A crude solution (reaction mixture) containing a 3-aminomethyl-3,5,5-trialkylcyclohexylamine obtained according to the hydrogenation reaction of the present invention can be subjected to a known purification such as distillation under reduced pressure to obtain the desired compound in a purified form.

The present invention will be further described by referring to the following examples, but the present invention should not be construed as being limited thereto.

"IPDA" indicates 3-aminomethyl-3,5,5-trimethylcyclohexylamine as the objective compound. "TAO" indicates 1,3,3-trimethyl-6-azabicyclo[3,2,1]octane as a by-product. "t-IPAN" indicates trans-3-cyano-3,5,5-trimethylcyclohexylamine as an intermediate of the objective compound.

IPDA occurs in the form of cis-isomer and trans-isomer. These isomers are derived from cis-3-cyano-3,5,5-trimethylcyclohexylamine (hereinafter referred to as "c-IPAN") and t-IPAN, respectively. TAO is produced from c-IPAN due to its structural characteristics, as illustrated in the following reaction mechanism. On the other hand, TAO and other by-products are not produced from t-IPAN. t-IPAN is a precursor all of which can be converted to IPDA if the reaction time is prolonged to carry through the reaction. Accordingly, t-IPAN is a useful product together with IPDA as the objective compound. t-IPAN and IPDA are thus defined as "valuable components".

$H_2O$) in 50 m$l$ of water. Water was then distilled off, and the carrier was then dried under reduced pressure. 14 m$l$ of a 1.7N aqueous solution of sodium carbonate was added to the material with stirring and then allowed to stand at room temperature for 1 hour. The carrier was washed with water, filtered off, and then dried under reduced pressure. The carrier was impregnated with a solution of 0.63 g of cobalt nitrate hexahydrate in 50 m$l$ of water. Water was distilled off, and the carrier was then dried under reduced pressure. The carrier was then reduced at a temperature of 300° C. in a stream of hydrogen to prepare a catalyst in which the amount of Ru was 5%, the amount of Co supported simultaneously with Ru was 1%, and the amount of Co supported separately from Ru was 1%, all based on the amount of the carrier, hereinafter referred to as (5%Ru-1%Co-1%Co added/SiO$_2$).

Ammonia Treatment of Starting Material 80 g of 3-cyano-3,5,5-trimethylcyclohexanone, 350 g of methanol, 150 g of ammonia and 20 g of triglym as an internal standard were charged into a 1,000-m$l$ induction agitating autoclave where they were then kept at a temperature of 40° C. for 2.5 hours and allowed to cool to room temperature.

Hydrogenation Reaction 48 g of the above mentioned ammonia-treated solution and 2.7 g of the above-prepared catalyst (5%Ru-

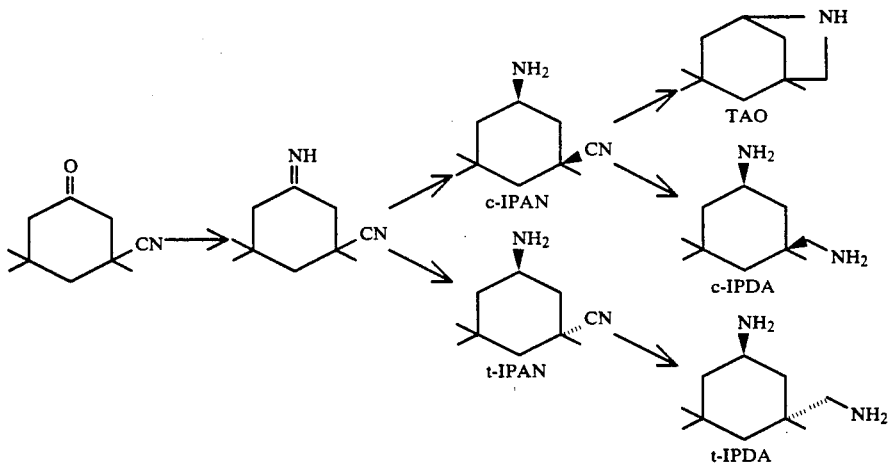

The percent TAO conversion as used in the following examples and comparative examples is represented by the following equation:

$$\text{TAO conversion (\%)} = \frac{(TAO)}{(c\text{-IPDA}) + (TAO)} \times 100$$

wherein (TAO) and (c-IPDA) represent the yield (mol%) of TAO and c-IPDA, respectively.

In the following Examples and Comparative Examples, all parts, percents and the like are by weight unless otherwise indicated.

EXAMPLE 1

Preparation of Catalyst 10 g of silica (SiO$_2$; "D-150-300A" produced by Dokai Kagaku K. K.) as a carrier was impregnated with a solution of 1.5 g of ruthenium chloride (RuCl$_3$·nH$_2$O) and 0.53 g of cobalt nitrate hexahydrate (Co(NO$_3$)$_2$·6-

1%Co-1%Co added/SiO$_2$) were charged into a 200-m$l$ induction agitating autoclave. The air in the autoclave was replaced by nitrogen gas. Hydrogen gas (room temperature) was then introduced into the autoclave at a pressure of 50 kg/cm$^2$·G. The autoclave was heated to a temperature of 120° C. At this point, hydrogen gas was further introduced into the autoclave in such an amount that the total pressure of the autoclave reached 100 kg/cm$^2$·G. The reaction mixture was allowed to undergo hydrogenation reaction for 1 hour while the system was kept at this pressure. After the completion of the reaction, the reaction system was allowed to cool to room temperature where the pressure thereof was then released. The resulting product solution was then analyzed by gas chromatography. The results are set forth in Table 1.

EXAMPLE 2

A catalyst (5%Ru-1%Co-2.5%Co added/SiO$_2$) was prepared in the same manner as in Example 1 except that the amount of cobalt additionally supported was changed to 2.5%. Using this catalyst, the hydrogenation reaction of 3-cyano-3,5,5-trimethylcyclohexanone was effected in the same manner as in Example 1. The results are set forth in Table 1.

EXAMPLE 3

A catalyst (5%Ru-2.5%Co-1%Co added/SiO$_2$) was prepared in the same manner as in Example 1 except that the amount of cobalt supported on the silica carrier simultaneously with ruthenium was changed to 2.5% and the concentration of the aqueous solution of sodium carbonate was changed to 2.1N. Using this catalyst, the hydrogenation reaction of 3-cyano-3,5,5-trimethylcyclohexanone was effected in the same manner as in Example 1. The results are set forth in Table 1.

EXAMPLE 4

A catalyst (5%Ru-1%Co-0%Co added/SiO$_2$) was prepared in the same manner as in Example 1 except that the amount of cobalt additionally supported was changed to 0%. Using this catalyst, the hydrogenation reaction of 3-cyano-3,5,5-trimethylcyclohexanone was effected in the same manner as in Example 1. The results are set forth in Table 1.

TABLE 1

|  | Example |  |  |  |
| --- | --- | --- | --- | --- |
|  | 1 | 2 | 3 | 4 |
| Amount of Ru supported (wt %) | 5 | 5 | 5 | 5 |
| Amount of Co supported simultaneously with Ru (wt %) | 1 | 1 | 2.5 | 1 |
| Amount of Co additionally supported (wt %) | 1 | 2.5 | 1 | 0 |
| Yield (mol %) |  |  |  |  |
| TAO | 8.2 | 7.9 | 8.5 | 13.8 |
| IPDA | 67.0 | 59.2 | 77.8 | 66.6 |
| t-IPAN | 15.1 | 16.7 | 5.3 | 8.7 |
| Valuable components IPDA + t-IPAN | 82.1 | 75.9 | 83.1 | 75.3 |
| TAO Conversion (%) | 12.8 | 13.4 | 12.7 | 20.9 |

EXAMPLE 5

A catalyst (5%Ru-0%Co-5%Co added/SiO$_2$) was prepared in the same manner as in Example 1 except that the amount of cobalt supported on the silica carrier simultaneously with ruthenium was changed to 0% and the concentration of the aqueous solution of sodium carbonate was changed to 1.4N. Using this catalyst, the hydrogenation reaction of 3-cyano-3,5,5-trimethylcyclohexanone was effected in the same manner as in Example 1. The results are set forth in Table 2.

EXAMPLE 6

A catalyst (5%Ru-5%Co-0%Co added/SiO$_2$) was prepared in the same manner as in Example 1 except that the amount of cobalt supported on the silica carrier simultaneously with ruthenium was changed to 5% and the concentration of the aqueous solution of sodium carbonate was changed to 2.9N. Using this catalyst, the hydrogenation reaction of 3-cyano-3,5,5-trimethylcyclohexanone was effected in the same manner as in Example 1. The results are set forth in Table 2.

TABLE 2

|  | Example |  |
| --- | --- | --- |
|  | 5 | 6 |
| Amount of Ru supported (wt %) | 5 | 5 |
| Amount of Co supported simultaneously with Ru (wt %) | 0 | 5 |
| Amount of Co additionally supported (wt %) | 5 | 0 |
| Yield (mol %) |  |  |
| TAO | 7.0 | 10.2 |
| IPDA | 70.0 | 70.3 |
| t-IPAN | 14.0 | 9.7 |
| Valuable components IPDA + t-IPAN | 84.0 | 80.0 |
| TAO Conversion (%) | 11.0 | 15.5 |

EXAMPLE 7

A catalyst (5%Ru-1%Co-5%Co added/SiO$_2$) was prepared in the same manner as in Example 1 except that the aqueous solution of sodium carbonate was replaced by 14 m$\iota$ of a 1.7N aqueous ammonia and the amount of cobalt additionally supported was changed to 5%.

Using this catalyst, the hydrogenation reaction of 3-cyano-3,5,5-trimethylcyclohexanone was effected in the same manner as in Example 1. The results are set forth in Table 3.

EXAMPLE 8

A catalyst (5%Ru-1%Co-0%Co added/SiO$_2$) was prepared in the same manner as in Example 1 except that the aqueous solution of sodium carbonate was replaced by 14 m$\iota$ of a 1.7N aqueous ammonia and the amount of cobalt additionally supported was changed to 0%. Using this catalyst, the hydrogenation reaction of 3-cyano-3,5,5-trimethylcyclohexanone was effected in the same manner as in Example 1. The results are set forth in Table 3.

TABLE 3

|  | Example |  |
| --- | --- | --- |
|  | 7 | 8 |
| Amount of Ru supported (wt %) | 5 | 5 |
| Amount of Co supported simultaneously with Ru (wt %) | 1 | 1 |
| Amount of Co additionally supported (wt %) | 5 | 0 |
| Yield (mol %) |  |  |
| TAO | 7.2 | 15.8 |
| IPDA | 68.5 | 71.1 |
| t-IPAN | 12.3 | 2.0 |
| Valuable components IPDA + t-IPAN | 80.8 | 73.1 |
| TAO Conversion (%) | 11.5 | 23.1 |

EXAMPLE 9

1.5 g of ruthenium chloride and 0.53 g of cobalt nitrate hexahydrate were dissolved in water to make 10.5 m$\iota$. The solution thus obtained was then sprayed over 10 g of silica (SiO$_2$; molded silica produced by Fuji Davison K. K.; "CARiACT-30.5-10 mesh") so that the carrier was impregnated with the solution. The carrier was then dried under reduced pressure. 10.5 m$\iota$ of a 2.4N aqueous solution of sodium hydroxide was then sprayed over the carrier with stirring. The carrier was then allowed to stand at room temperature for 1 hour. The carrier was washed with water, and then dried under reduced pressure. With 220 m$\iota$ of a 0.4M aqueous formalin added, the carrier was then pre-reduced at a temperature of 60° C. for 1 hour. The carrier was washed with water at 60° C., and then dried under reduced pressure.

1.33 g of cobalt nitrate hexahydrate was dissolved in water to make 10.5 m$\iota$. The solution thus obtained was sprayed over the carrier so that the carrier was impregnated with the solution to additionally have cobalt supported thereon. The carrier was then dried under reduced pressure. The carrier was reduced at a temperature of 300° C. in a stream of hydrogen to prepare a molded catalyst (5%Ru-1%Co-2.5%Co added/SiO$_2$).

The hydrogenation reaction of 3-cyano-3,5,5-trimethylcyclohexanone was effected in the same manner as in Example 1 except that 3.7 g of the molded catalyst thus obtained was used. The results are set forth in Table 4.

EXAMPLE 10

A catalyst (5%Ru-1%Co-5%Co added/SiO$_2$) was prepared in the same manner as in Example 9 except that the amount of cobalt additionally supported was changed to 5%. Using this catalyst, the hydrogenation reaction of 3-cyano-3,5,5-trimethylcyclohexanone was effected in the same manner as in Example 9. The results are set forth in Table 4.

EXAMPLE 11

A catalyst (5%Ru-1%Co-5%Co added/SiO$_2$) was prepared in the same manner as in Example 9 except that the washing with water after the pre-reduction with aqueous formalin was effected under reflux, cobalt acetate (II) was used as a source of cobalt additionally supported and the amount of cobalt additionally supported was changed to 5%. Using this catalyst, the hydrogenation reaction of 3-cyano-3,5,5-trimethylcyclohexanone was effected in the same manner as in Example 9. The results are set forth in Table 4.

EXAMPLE 12

A catalyst (5%Ru-5%Co-0%Co added/SiO$_2$) was prepared in the same manner as in Example 9 except that the amount of cobalt supported simultaneously with ruthenium was changed to 5% and the amount of cobalt additionally supported was changed to 0%. Using this catalyst, the hydrogenation reaction of 3-cyano-3,5,5-trimethylcyclohexanone was effected in the same manner as in Example 9. The results are set forth in Table 4.

EXAMPLE 13

A catalyst (5%Ru-2.5%Co-10%Co added/SiO$_2$) was prepared in the same manner as in Example 9 except that the amount of cobalt supported simultaneously with ruthenium was changed to 2.5% and the amount of cobalt additionally supported was changed to 10%. Using this catalyst, the hydrogenation reaction of 3-cyano-3,5,5-trimethylcyclohexanone was effected in the same manner as in Example 9. The results are set forth in Table 5.

TABLE 4

| | Example | | | | |
|---|---|---|---|---|---|
| | 9 | 10 | 11 | 12 | 13 |
| Amount of Ru supported (wt %) | 5 | 5 | 5 | 5 | 5 |
| Amount of Co supported simultaneously with Ru (wt %) | 1 | 1 | 1 | 5 | 2.5 |
| Amount of Co additionally supported (wt %) | 2.5 | 5 | 5 | 0 | 10 |
| Yield (mol %) | | | | | |
| TAO | 6.2 | 5.7 | 7.1 | 9.8 | 8.2 |
| IPDA | 75.8 | 78.8 | 83.8 | 76.7 | 82.7 |
| t-IPAN | 10.4 | 4.0 | 1.6 | 2.2 | 0.3 |
| Valuable components IPDA + t-IPAN | 86.2 | 82.8 | 85.4 | 78.9 | 83.0 |
| TAO Conversion (%) | 9.5 | 9.1 | 10.4 | 14.4 | 12.1 |

EXAMPLE 14

2.66 g of cobalt nitrate hexahydrate was dissolved in water to make 10.5 m$\iota$. The solution thus obtained was then sprayed over 10 g of silica (SiO$_2$; molded silica produced by Fuji Davison K. K.; "CARiACT-30.5-10 mesh") so that the carrier was impregnated with the solution. The carrier was then dried under reduced pressure. The carrier was calcined at a temperature of 300° C. in a stream of air for 2 hours. 1.5 g of ruthenium chloride was dissolved in water to make 10.5 m$\iota$. The solution thus obtained was then sprayed over the carrier with stirring so that the carrier was impregnated with the solution. The carrier was then dried under reduced pressure. 10.5 m$\iota$ of a 1.8N aqueous solution of sodium hydroxide was then sprayed over the carrier. The carrier was then allowed to stand at room temperature for 1 hour. The carrier was washed with water, and then dried under reduced pressure. With 220 m$\iota$ of a 1.0M aqueous formalin added, the carrier was then pre-reduced at a temperature of 60° C. for 1 hour. The carrier was washed with water under reflux of water, and then dried under reduced pressure. The carrier was then reduced at a temperature of 300° C. in a stream of hydrogen to prepare a molded catalyst (5%Co-5%Ru added/SiO$_2$). The hydrogenation reaction of 3-cyano-3,5,5-trimethylcyclohexanone was effected in the same manner as in Example 1 except that 3.7 g of the molded catalyst thus obtained was used. The results are set forth in Table 5.

EXAMPLE 15

2.66 g of cobalt nitrate hexahydrate and 1.5 g of ruthenium chloride were dissolved in water to make 10.5 m$\iota$. The solution thus obtained was then sprayed over 10 g of silica (SiO$_2$; molded silica produced by Fuji Davison K. K.; "CARiACT-30.5-10 mesh") so that the carrier was impregnated with the solution. The carrier was then dried under reduced pressure. 10.5 m$\iota$ of a 3.7N aqueous solution of sodium hydroxide was then sprayed over the carrier with stirring. The carrier was then allowed to stand at room temperature for 1 hour. The carrier was washed with water, and then dried under reduced pressure. With 220 m$\iota$ of a 1.0M aqueous formalin added, the carrier was then pre-reduced at a temperature of 60° C. for 1 hour. The carrier was washed with water under reflux of water, and then dried under reduced pressure. The carrier was then reduced at a temperature of 300° C. in a stream of hydrogen to prepare a molded catalyst (5%Co-5%Ru/SiO$_2$). The hydrogenation reaction of 3-cyano-3,5,5-trimethylcyclohexanone was effected in the same manner as in Example 1 except that 3.7 g of the molded catalyst thus obtained was used. The results are set forth in Table 5.

TABLE 5

|  | Example | |
|---|---|---|
|  | 14 | 15 |
| Amount of Ru supported (wt %) | 5 | 5 |
| Amount of Co supported | 5 | 5 |
| Supporting method | After supporting Co, Ru was supported. | Co and Ru were simultaneously supported. |
| Yield (mol %) | | |
| TAO | 7.1 | 14.8 |
| IPDA | 79.7 | 79.3 |
| t-IPAN | 5.9 | 0.2 |
| Valuable components IPDA + t-IPAN | 85.6 | 79.5 |
| TAO Conversion (%) | 10.7 | 19.4 |

In the resulting product solutions obtained in the above Examples 1 to 15, a trace amount of 3,3,5-trimethylcyclohexylamine, 3-aminomethyl-3,5,5-trimethylcyclohexanol and amidine (cyclized isomer of IPAN) were contained.

EXAMPLE 16

10 g of silica (D-150-300A produced by Dokai Kagaku K. K.) as a carrier was impregnated with a solution of 1.5 g of ruthenium chloride ($RuCl_3 \cdot 3H_2O$) and 2.66 g of cobalt nitrate ($Co(NO_3)_2 \cdot 6H_2O$) in 50 m$\iota$ of water. The carrier was dried, and then reduced at a temperature of 200° C. in a stream of hydrogen to prepare a catalyst (5%Ru-5%Co/$SiO_2$).

8 g of 3-cyano-3,5,5-trimethylcyclohexanone, 35.7 g of methanol and 15 g of ammonia were charged into a 200-m$\iota$ induction agitating autoclave. The reaction system was processed at a temperature of 40° C. for 3.5 hours, and then allowed to cool to room temperature. In an atmosphere of Ar, the autoclave was opened, and 2.4 g of the above mentioned catalyst (5%Ru-5%Co/$SiO_2$) was then added to the reaction system. The gas in the autoclave was replaced by an inert gas. Hydrogen gas was charged into the autoclave at room temperature at a pressure of 50 kg/$cm^2$·G. The reaction system was then heated to a temperature of 120° C. When the temperature of the reaction system reached 120° C., hydrogen gas was pressed into the autoclave in such a manner that the total pressure therein reached 100 kg/$cm^2$·G, and the reaction system was then allowed to undergo reaction for 1 hour. The autoclave was allowed to cool. The pressure of the autoclave was then released. The resulting product solution was withdrawn and then analyzed by gas chromatography. As a result, it was found that 3-aminomethyl-3,5,5-trimethylcyclohexylamine, 3-aminomethyl-3,5,5-trimethylcyclohexanol (hereinafter referred to as "IPAA") and 1,3,3-trimethyl-6-azabicyclo[3,2,1]octane had been produced at yields of 82.4%, 5.2% and 8.2%, respectively.

COMPARATIVE EXAMPLE 1

A reaction was effected in the same manner in Example 16 except that the catalyst (5%Ru-5%Co/$SiO_2$) was replaced by 2.7 g of a catalyst (5%Ru/$SiO_2$) prepared in the same manner as in Example 17. As a result, IPDA, IPAA and TAO were produced at yields of 74.8%, 4.8% and 13.0%.

EXAMPLE 17

A reaction was effected in the same manner in Example 16 except that the catalyst (5%Ru-5%Co/$SiO_2$) was replaced by 2.3 g of a catalyst (5%Ru-2.5%Co/$SiO_2$) prepared in the same manner as in Example 17. As a result, IPDA, IPAA and TAO were produced at yields of 77.1%, 4.9% and 8.2%.

EXAMPLE 18

8 g of 3-cyano-3,5,5-trimethylcyclohexanone, 35 g of 1-methoxy-2-propanol and 15 g of ammonia were charged into a 200-m$\iota$ induction agitating autoclave. The reaction system was allowed to undergo reaction at a temperature of 40° C. for 3.5 hours. The reaction system was allowed to cool to room temperature. In an atmosphere of Ar, the autoclave was opened, and 2.3 g of a catalyst (5%Ru-2.5%Co/$SiO_2$) prepared in the same manner as in Example 16 was then added to the reaction system. The gas in the autoclave was replaced by an inert gas. 7.8 g of ammonia was then added to the reaction system. Hydrogen gas was pressed into the autoclave in such a manner that the total pressure therein reached 50 kg/$cm^2$·G. The reaction system was then heated to a temperature of 120° C. When the temperature of the reaction system reached 120° C., hydrogen gas was pressed into the autoclave in such a manner that the total pressure therein reached 100 kg/$cm^2$·G where the reaction was started. After one hour of reaction, the reaction solution was withdrawn and then analyzed. As a result, it was found that IPDA, IPAA and TAO had been produced at yields of 80.0%, 4.0% and 8.5%, respectively.

EXAMPLE 19

A reaction was effected in the same manner in Example 18 except that the solvent 1-methoxy-2-propanol was replaced by 35 g of tetraethylene glycol and the hydrogenation reaction time was changed to 2 hours. As a result, IPDA, IPAA and TAO were produced at yields of 82.9%, 3.2% and 6.6%, respectively.

EXAMPLE 20

8 g of 3-cyano-3,5,5-trimethylcyclohexanone, 35.7 g of methanol and 2.7 g of a catalyst (5%Ru-2.5%Co/$SiO_2$) prepared in the same manner as in Example 16 were charged into a 200-m$\iota$ induction agitating autoclave. The gas in the autoclave was replaced by an inert gas. 2.0 g of ammonia and hydrogen gas were pressed into the autoclave in such a manner that the total pressure therein reached 50 kg/$cm^2$·G. The reaction system was then heated to a temperature of 120° C. When the temperature of the reaction system reached 120° C., hydrogen gas was further pressed into the autoclave in such a manner that the total pressure therein reached 100 kg/$cm^2$·G where the reaction was started. After one hour of reaction, it was found that IPDA, IPAA and TAO had been produced at yields of 69.6%, 24.3% and 5.2%, respectively.

COMPARATIVE EXAMPLE 2

A reaction was effected in the same manner in Example 20 except that the catalyst (5%Ru-2.5%Co/$SiO_2$) as used in Example 21 was replaced by 2.7 g of a catalyst (5%Ru/$SiO_2$). As a result, IPDA, IPAA and TAO were produced at yields of 66.8%, 19.4% and 7.9%, respectively.

COMPARATIVE EXAMPLE 3

A reaction was effected in the same manner as in Example 21 except that 2.2 g of a catalyst obtained by reducing a commercial Co/$SiO_2$ catalyst ("G-61RS" available from Nissan Guardler) in the presence of hydrogen at a temperature of 200° C. for 2 hours and 6.5 g of ammonia were used. IPDA was obtained at a yield of only 0.6%.

In the present invention, the use of a catalyst with a relatively easy handling enables the production of 3-aminomethyl-3,5,5-trialkylcyclohexylamine under simple operation conditions and reaction conditions which are mild as compared with the prior art. The process of the present invention can reduce the production of 1,3,3-trimethyl-6-azabicyclo[3,2,1]octane and the like as by-products.

While the invention has been described in detail and with reference to specific embodiments thereof, it will be apparent to one skilled in the art that various changes and modifications can be made therein without departing from the spirit and scope thereof.

What is claimed is:

1. A process for the preparation of a 3-aminomethyl-3,5,5-trialkylcyclohexylamine, which comprises hydrogenating 3-cyano-3,5,5-trialkylcyclohexanone in the presence of ammonia and a ruthenium-cobalt catalyst.

2. A process as claimed in claim 1, wherein said ruthenium-cobalt catalyst is a supported ruthenium-cobalt catalyst.

3. A process as claimed in claim 2, wherein said supported ruthenium-cobalt catalyst comprises ruthenium and cobalt supported on an inorganic porous carrier.

4. A process as claimed in claim 3, wherein said inorganic porous carrier is silica.

5. A process as claimed in claim 2, wherein said supported ruthenium-cobalt catalyst is obtained by impregnating a carrier with ruthenium and cobalt and then fixing said components thereon.

6. A process as claimed in claim 5, wherein said fixing is effected by treating the material with an alkaline solution or calcining the material in an atmosphere of oxygen-containing gas.

7. A process as claimed in claim 2, wherein the alkyl group contained in 3-cyano-3,5,5-trialkylcyclohexanone is an alkyl group having 1 to 6 carbon atoms.

8. A process as claimed in claim 2, wherein said supported ruthenium-cobalt catalyst is used in an amount of 5 to 30% by weight based on the weight of 3-cyano-3,5,5-trialkylcyclohexanone.

9. A process as claimed in claim 2, wherein ammonia is used in an amount of 1 to 50 times by mol the amount of 3-cyano-3,5,5-trialkylcyclohexanone.

10. A process as claimed in claim 2, wherein the hydrogenation is effected at a reaction pressure of 20 to 150 atm.

11. A process as claimed in claim 10, wherein the hydrogenation is effected at a reaction pressure of 50 to 100 atm.

12. A process as claimed in claim 2, wherein the hydrogenation is effected at a reaction temperature of 50 to 150° C.

13. A process as claimed in claim 2, wherein the hydrogenation is effected in the presence of a solvent.

14. A process as claimed in claim 13, wherein said solvent is used in an amount of 1 to 10 times by weight that of 3-cyano-3,5,5-trialkylcyclohexanone.

15. A process as claimed in claim 2, wherein said supported ruthenium-cobalt catalyst is prepared by having cobalt supported on a carrier before or after ruthenium is supported or ruthenium and cobalt are simultaneously supported thereon.

16. A process as claimed in claim 15, wherein the amount of cobalt supported on said carrier separately from ruthenium is larger than the amount of cobalt to be supported on the carrier simultaneously with ruthenium.

17. A process as claimed in claim 2, wherein said supported ruthenium-cobalt catalyst comprises ruthenium and cobalt supported on a carrier in a total amount of 0.1 to 40% by weight based on the weight of catalyst as calculated in terms of metal.

18. A process as claimed in claim 2, wherein the weight proportion of cobalt to ruthenium in said supported ruthenium-cobalt catalyst is in the range of 0.1 to 20.

19. A process as claimed in claim 18, wherein the weight proportion of cobalt to ruthenium in said supported ruthenium-cobalt catalyst is in the range of 0.3 to 10.

* * * * *